Nov. 26, 1963 C. FISCHER Plant Pat. 2,318
GLADIOLUS PLANT
Filed July 5, 1962
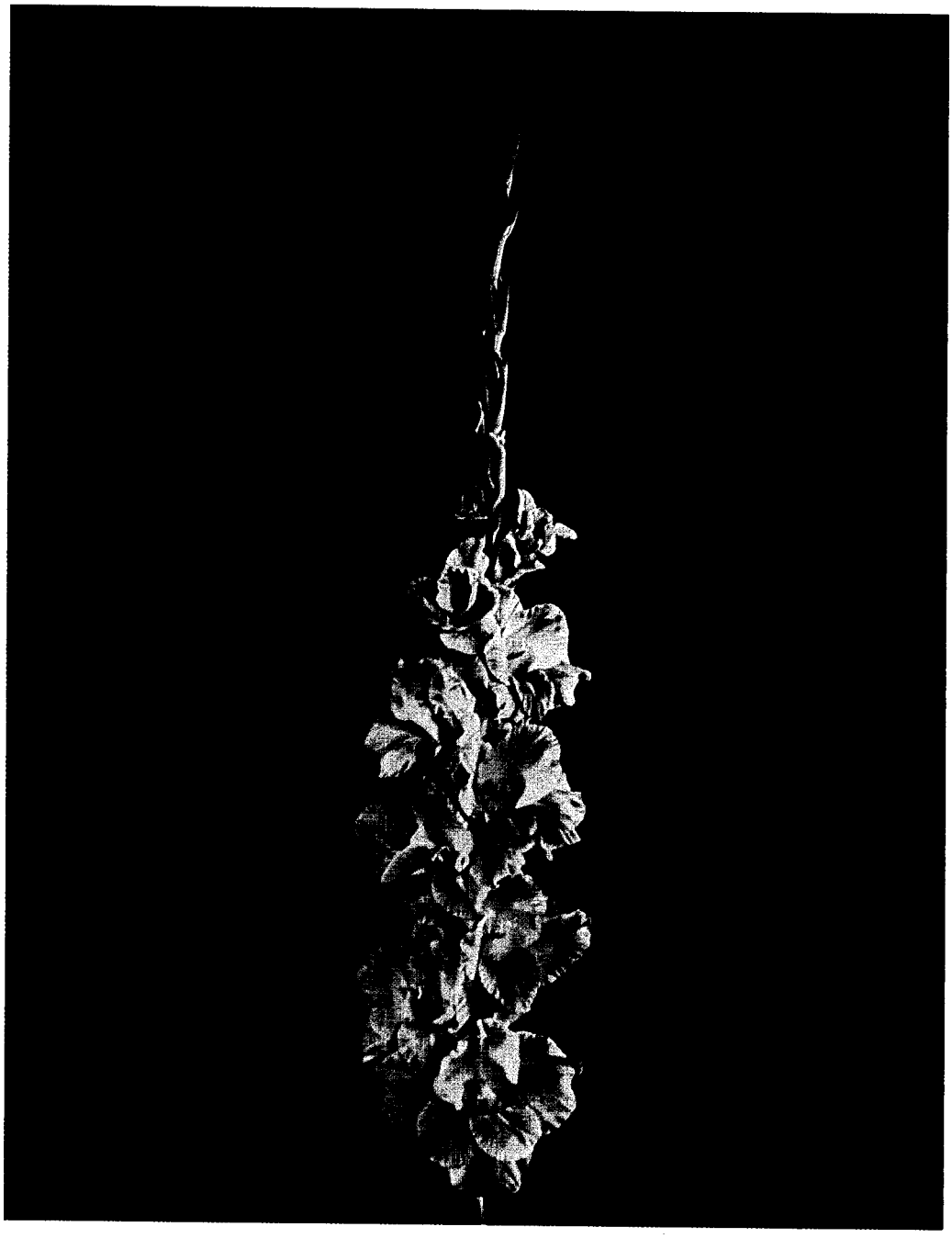
Inventor
Carl Fischer
By: Robb & Robb
Attorneys.

United States Patent Office

Plant Pat. 2,318
Patented Nov. 26, 1963

2,318
GLADIOLUS PLANT

Carl Fischer, St. Charles, Minn., assignor to Imperial Flowers Limited, Leamington, Ontario, Canada, a corporation of Canada Filed July 5, 1962, Ser. No. 207,832
1 Claim. (Cl. Plt.—85)

The present invention relates to a new and distinct variety of gladiolus plant which was originated by me by crossing two unnamed and unpatented gladiolus varieties of unidentified parentage, said cross having been made by me by manual cross pollination as performed in my outdoor breeding fields at St. Charles, Minnesota.

As the result of this breeding, I have produced a new and improved gladiolus variety which is distinguished from its parents, as well as from all other varieties of which I am aware, as evidenced by the following unique combination of characteristics which are outstanding therein:

(1) A substantially uniform habit of growth;
(2) A relatively early blooming habit; and
(3) A distinctive and attractive pink or rose general color tonality of the flowers, with a silver picotee edging on the petals of the individual florets.

My new variety resembles the variety known as "Chamouny" (unpatented) more than any other, but differs principally therefrom and from other varieties in this color range by being healthier and a better propagator; an earlier bloomer; a more tapering flower head; a more elegant flower form; a more intense ruffling of the flower petals; and a more uniform flower color.

Asexual reproduction of my new variety by cormels through several generations, as performed by me at St. Charles Minnesota, shows that the foregoing characteristics and distinctions come true to form and are established and transmitted through succeeding propagations.

The accompanying drawing shows a typical specimen flower spike of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations by plantings derived from cormels.

*Plant*

Growth: Vigorous; propagates very well; blossom spike averages from 50 inches to 56 inches high.

Blooming habit: An early bloomer in the Northern latitudes of the United States; comes into bloom from large bulbs in about 70 days.

Stems: Willowy.

*Diameter at base.*—½ inch.

*Color (just above the bulb).*—Ranges between Orchid Purple, Plate 31/3 and Orchid Purple, Plate 31/2.

Foliage: Slightly drooping; leaves average from about 1¼ inches to 1½ inches wide; leaves attain height of about 34 inches.

Disease resistance: Average resistance to Fusarium yellows and Sclerotina dry rot, but better resistance to Septoria leaf spot, as determined by comparison with other varieties grown in my fields near St. Charles, Minnesota, in irrigated black loam soal.

Corms (bulbs): Healthy; plum; average 2 inches in diameter from adult plants; rough husks, but do not always completely cover the corms, with husks having a purplish cast. Color of flesh—slightly tinted with a purplish cast.

*Flower*

Spike: Tall; slender; bears 17 or 18 buds, with from 2 to 4 florets opening on the first day, followed by from 6 to 9 opening at one time, with 5 or 6 buds showing color above the open florets.

Bud:

*Size.*—From 2½ inches to 3 inches long when opening.

*Opening*—Opens well.

Flower:

*Arrangement.*—Florets are informally arranged on the stem and consistently face forward.

*Size.*—Lower florets average 5¼ inches in diameter when permitted to bloom on the plant in the field, with upper florets being progressively smaller.

*Form.*—Open wide; ruffled.

*Keeping qualities.*—Keeps well.

Petals:

*Shape.*—Ruffled; slightly triangular.

*Size.*—Upper petals—about 2½ inches wide. Lip petal—about 1½ inches wide.

*Aspect.*—Average substance; smooth surface; ruffled; picoteed at edges.

*Fragrance.*—None

*Color.*—Upper petals—Neyron Rose, Plate 623/1, shading to Neyron Rose, Plate 623/2 toward lightest area at edges, giving silver picotee appearance on edges. Lip petals—ranging between Phlox Pink, Plate 625 to Phlox Pink, Plate 625/1, with picotee edging to Neyron Rose, Plate 623/2.

*Reproductive organs*

Stamens: Color—Light Purple.

Pistil:—Color—Neyron Rose.

I claim:

A new and distinct variety of gladiolus plant, substantially as herein shown and described, characterized particularly as to novelty by the unique combination of a substantially uniform habit of growth, a relatively early blooming habit, and a distinctive and attractive pink or rose general color tonality of the flowers, with a silver picotee edging on the petals of the individual florets.

No references cited.